(12) United States Patent
Luce (10) Patent No.: US 10,779,985 B2
(45) Date of Patent: Sep. 22, 2020

(54) ADAPTER INSERT FOR AN OSTOMY GUARD

(71) Applicant: Donna E. Luce, Duncanville, TX (US)

(72) Inventor: Donna E. Luce, Duncanville, TX (US)

( * ) Notice: Subject to any disclaimer, the term of this patent is extended or adjusted under 35 U.S.C. 154(b) by 678 days.

(21) Appl. No.: 15/582,639

(22) Filed: Apr. 29, 2017

(65) Prior Publication Data

US 2017/0231802 A1   Aug. 17, 2017

Related U.S. Application Data

(62) Division of application No. 13/874,283, filed on Apr. 30, 2013, now Pat. No. 10,617,554.

(51) Int. Cl.
| | |
|---|---|
| A61F 5/44 | (2006.01) |
| A61F 5/441 | (2006.01) |
| A61F 5/448 | (2006.01) |
| A61F 5/443 | (2006.01) |

(52) U.S. Cl.
CPC .............. *A61F 5/441* (2013.01); *A61F 5/443* (2013.01); *A61F 5/4408* (2013.01); *A61F 5/448* (2013.01)

(58) Field of Classification Search
CPC ........ A61F 5/4408; A61F 5/441; A61F 5/443; A61F 5/448
See application file for complete search history.

(56) References Cited

U.S. PATENT DOCUMENTS

| | | |
|---|---|---|
| 1,922,763 A | 8/1933 | Gricks |
| 2,129,054 A | 9/1938 | Geisler |
| 2,496,175 A | 1/1950 | Perry |
| 2,549,649 A | 4/1951 | Hove |
| 2,656,838 A | 10/1953 | McConnell |
| 2,675,002 A | 4/1954 | Cesare |
| 2,837,094 A | 6/1958 | Cowles |
| 3,074,404 A | 1/1963 | Robinson |
| 3,398,744 A | 8/1968 | Hooper |
| 4,596,566 A | 6/1986 | Kay |
| 4,636,206 A | 1/1987 | Ederati et al. |
| 4,723,952 A | 2/1988 | Esposito |
| 4,738,257 A | 4/1988 | Meyer et al. |
| 4,867,749 A | 9/1989 | Steer |
| 5,125,917 A | 6/1992 | Whealin |
| 5,178,614 A | 1/1993 | McDowell et al. |
| 5,257,981 A * | 11/1993 | Takahashi .............. A61F 5/448 604/332 |
| 5,338,315 A | 8/1994 | Baker |

(Continued)

FOREIGN PATENT DOCUMENTS

WO         9716141 A1    5/1997

*Primary Examiner* — Kai H Weng
(74) *Attorney, Agent, or Firm* — SMU Law School Patent Clinic (57) ABSTRACT

An adapter insert is for the purpose of reinforcing or stiffening a flexible adapter for said guard system to provide greater support and stabilization in the peristomal region in an effort to help reduce herniation, and to help aid adhesion of a faceplate when worn short term without a guard when output is expected to be minimal, for instance, between meals. The conjoined insert and adapter are positioned between a faceplate and a pouch, their inner apertures surrounding the faceplate flanges or heat weld of an ostomy appliance, and worn under form-fitted clothing negating the need for a security strap.

10 Claims, 9 Drawing Sheets

(56) References Cited

U.S. PATENT DOCUMENTS

| | | | |
|---|---|---|---|
| 5,653,701 | A | 8/1997 | Millman |
| 5,811,116 | A | 9/1998 | Gilman et al. |
| 5,989,235 | A | 11/1999 | Quacquarella et al. |
| 6,129,715 | A | 10/2000 | Cunningham |
| 8,316,985 | B2 | 11/2012 | Bain et al. |
| 2002/0032418 | A1 | 3/2002 | Iseke |
| 2007/0129695 | A1 | 6/2007 | Blum |
| 2007/0135783 | A1 | 6/2007 | Scott |
| 2010/0191202 | A1 | 7/2010 | Hogard et al. |
| 2010/0241093 | A1 | 9/2010 | Hooper |

\* cited by examiner

ADAPTER INSERT FOR AN OSTOMY GUARD

CROSS REFERENCE TO RELATED APPLICATIONS

This application is a divisional of application Ser. No. 13/874,283, filed Apr. 30, 2013, the entirety of which is incorporated herein by reference for all purposes.

STATEMENT REGARDING FEDERALLY SPONSORED RESEARCH OR DEVELOPMENT

Not applicable

TECHNICAL FIELD

This invention relates generally to systems for securing ostomy waste collection pouches to the body and preventing leakage of primary securement means.

BACKGROUND OF THE INVENTION

Ileostomies, colostomies, and urostomies are surgically created openings in which a portion of the intestine is brought through the abdominal wall to form a stoma, which may be permanent or temporary depending on the reason for surgery, i.e. disease, injury, birth defects or cancer. A pouching system or 'appliance,' as it is sometimes referred to, is used to collect waste material. Pouch styles and sizes vary from manufacturer to manufacturer, however, two main types of pouching systems are available: one-piece pouches with a built in skin barrier (faceplate), and two piece systems comprised of a faceplate and detachable pouch.

The two-part system provides a flange in the form of a pair of annular or ring-like rigid plastic parts designed to aid in either securing the pouch to the faceplate or removing the pouch at the user's discretion. Faceplates are further comprised of an adhesive layer formed of a soft, skin-friendly hydrocolloid containing adhesive material and provide therein a centrally located aperture to receive a stoma. Systems may further provide a peel and stick tape on the outer edges of a faceplate for additional adhesion. These faceplates are attached to the peristomal region of the user to protect the skin from irritating digestive juices. A convex faceplate is generally used when a stoma protrudes less than an inch and a flat faceplate is generally used when a stoma protrudes more than an inch.

Preoperative preparation for a stoma creation includes selection of the most optimal site and consideration is taken not only for skin creases, prior scars, and any bony prominences, but is also based on whether a patient has a flat, muscular abdomen, or an obese abdomen to allow for proper visualization and care. One problem, despite careful planning and individualized considerations, is that pressure from a waistband of jeans or clothing contacting or lying across any part of a faceplate can interfere with the quality of the seal and adherence to the skin of the user threatening a resulting loss of containment. Many other factors influence how long a pouching system will stay sealed. Subsequent leakage of waste can and does occur, often without warning, soiling clothes, causing unpleasant odors and embarrassment to the wearer.

Another problem faced by ostomates are parastomal hernias. Online research indicates that hernia is essentially caused by expansion of the stoma trephine aperture in the abdominal wall resulting from tangential pressure on the circumference of the opening, often gradually through the passage of time. Ideally, the stoma is brought through the rectus abdominus muscle (six pack muscle) that lies vertically adjacent one's belly button to reduce the likelihood of a hernia or stomal prolapse but bringing the stoma to the surface of the abdomen immediately creates a weakness and a potential for hernia. Coughing, sneezing, infection from surgery, obesity, weak muscles and the strain upon rising or sitting can cause a bulging at the stoma site with the potential for the muscle or skin of the abdomen to come away from the stoma creating a passageway for the viscera to protrude.

The size of the hernia generally increases with time, is often uncomfortable and is an embarrassment as its increased size can be seen under clothing and furthermore, it becomes difficult to attach a pouching system properly thereby causing peristomal skin breakdown. A trapped or twisted portion of intestine within the hernia may become obstructed or strangulated and may require emergency surgery to repair. Complicating matters are those who may be elderly, frail, or those for whom an anesthetic would be dangerous because of breathing or heart problems, are at great risk to undergo surgery for repair of the hernia. If the hernia is not causing any symptoms, a wide, firm hernia belt is suggested management. Although these factors are not a comprehensive list of complications, several online medical reports maintain that development of parastomal hernias are nearly an inevitable complication following formation of a stoma.

If hernia symptoms are severe, or to improve quality of life for an ostomate, methods of hernia repair may include resiting the stoma to a new location, which is a major operation to take down and transfer the stoma from one side to the other. Hernia repair without resiting the stoma may involve opening the adjacent abdominal wall to re-suture muscle and supporting tissues in the area either thru laparotomy or laparascopically. The use of mesh over and beyond the weakened area has been an alternative approach as well as prosthetic devices to keep the mesh from enlarging are used as adjunct to local repair of paracolostomy hernia.

Psychological struggles are another problem faced by ostomates. Although creation of a stoma is often a life-saving operation, many ostomates fear that others may notice the pouching system or a growing hernia under their clothing, or that a leak in public will cause embarrassment and humiliation resulting in isolation.

SUMMARY OF THE INVENTION

Herein disclosed are adapter inserts for the purpose of reinforcing or stiffening a flexible adapter for a guard system to provide greater support and stabilization in the peristomal region in an effort to help reduce herniation, and to help aid adhesion of a faceplate when worn short term without a complementary guard, while allowing a more sleek profile under clothing when output is expected to be minimal, for instance, between meals. The conjoined insert and adapter are worn between a faceplate and a pouch, their inner aperture surrounding the faceplate flanges of an ostomy appliance (or the heat weld of a one-piece appliance) under form-fitted clothing negating the need for a security strap.

DETAILED DESCRIPTION

Herein disclosed are inserts for an adapter, the adapter being described in a previous application No. 61/506,484 describing a guard system comprising a guard and adapter for an ostomate utilizing a two-piece or one-piece ostomy pouching system (appliance) of the type secured to the body with a faceplate.

Figure 1:
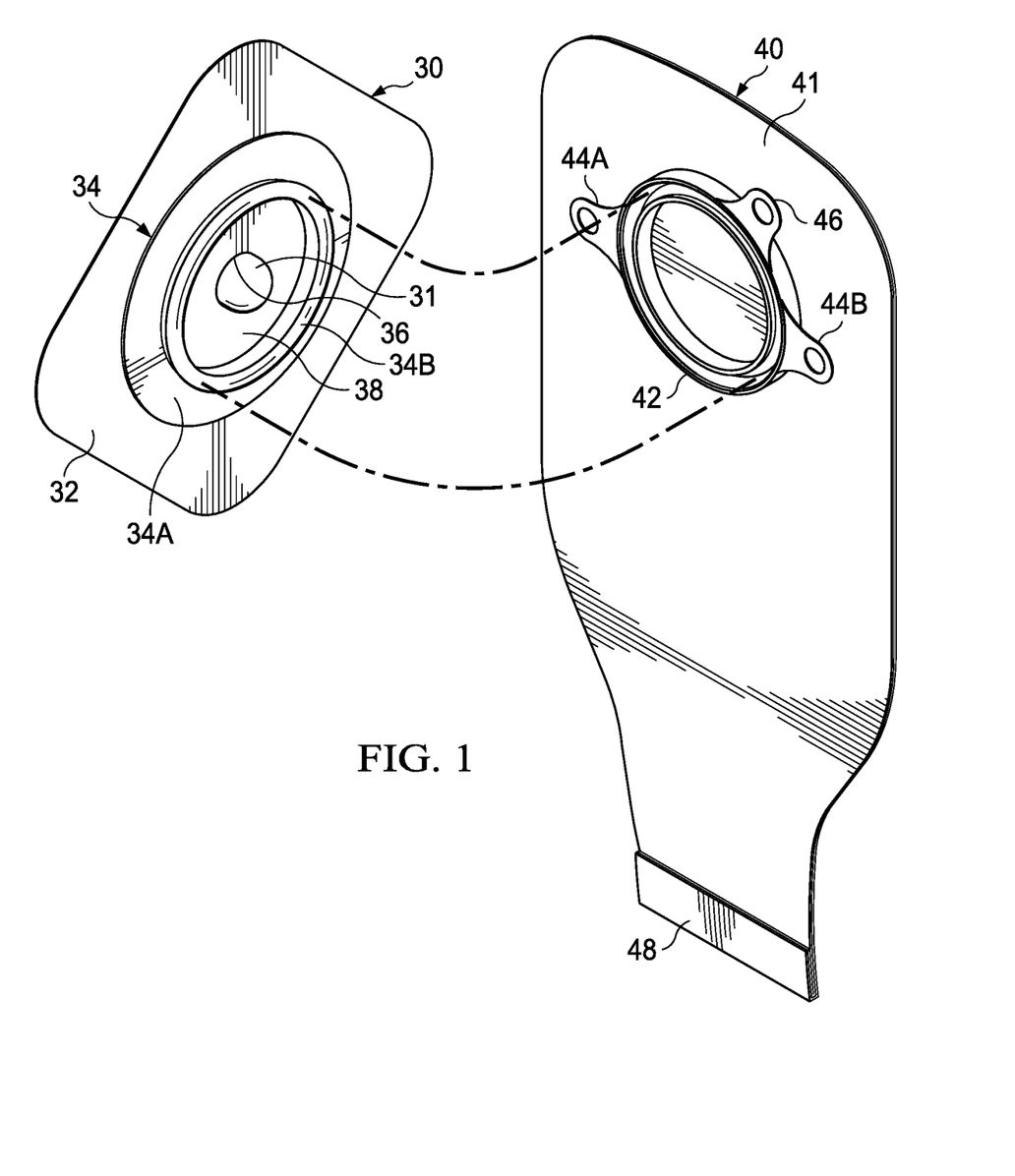
FIG. 1 is a perspective view of an exemplary two-piece ostomy appliance comprising a pouch and a faceplate.
Figure 2:
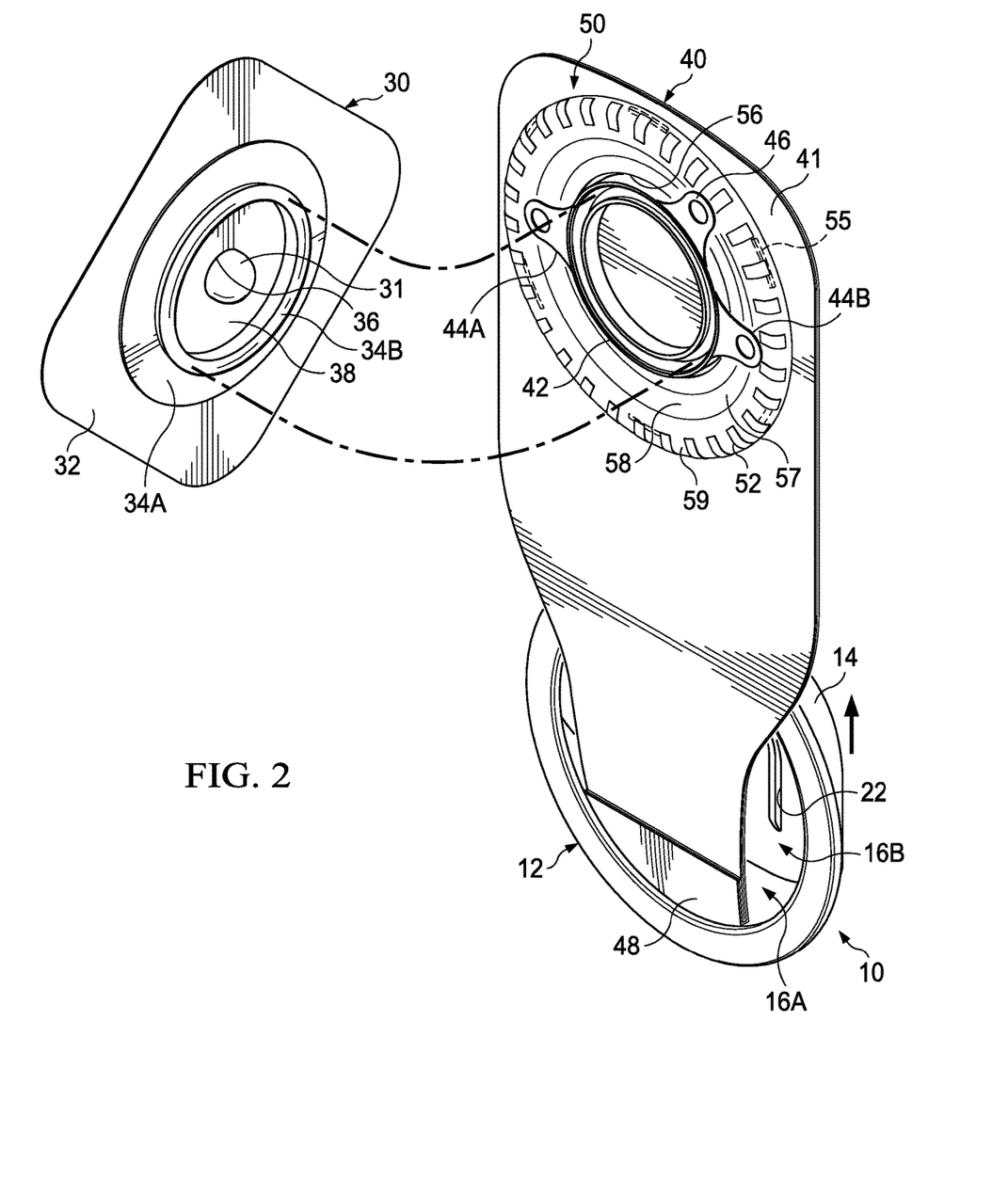
FIG. 2 is a perspective view of a two-piece ostomy appliance of FIG. 1 and guard system.

The illustration of FIGS. 1 and 2 are given to allow for visual understanding of an ostomy appliance system and a guard system and are not the inventions of the present application.

One such example of an appliance is illustrated in FIG. 1 and is a typical example of a current, commercially available two-piece ostomy pouching system consisting of a pouch 40, a pouch flange 42, belt tabs 44A and 44B on either side of the pouch flange; a tab on the upper flange facilitates easy removal, and a fold and lock drain 48 for removal of waste. The two-piece appliance also consists of a faceplate 30, with coupling flange 34B and centrally located aperture 36 to receive a stoma 31. An outer taped portion 32 aids adhesion of an appliance faceplate on the abdomen.

The ostomy appliance guard system illustrated in FIG. 2 is comprised of a guard 10 and an adapter 50. The adapter 50 is provided in various sizes in the centrally located aperture 56 to accommodate the various flange sizes of ostomy appliances currently available, and allows the guard 10 to remain a universal size. Appliance flanges are provided in common sizes between appliance manufacturers, but are not necessarily interchangeable. The adapter 50, shown already in place, illustrates that flange 42 of pouch 40 is snapped into place with complementary flange 34B of a faceplate 30.

The adapter 50 applied first, having the pouch end 48 guided through the rear of centrally located aperture 56, is lifted up and over the upper portion of a pouch 41, and aperture 56 is then circumferentially surrounding the now coupled appliance flanges 42 and 34B. Adapter support wall 58, pressing inwardly on flange base 34A, helps a stoma to protrude while preventing the flanges 42/34B from protruding into the body of the guard 10. Pouch tabs 44A, 44B and 46 may be removed for more efficient use of the guard system 10/50.

The guard 10 is applied in the same manner as adapter 50, and pouch end 48 is guided through rear central aperture 16B of guard 10, then out through front aperture 16A, the arrow indicates that guard 10 is then lifted upwards until body 14 of guard 10 encompasses the now engaged flanges including the upper pouch portion 41 (tucked inside guard body in use to prevent intestinal gasses from ballooning above a waistline of pants), and annular ring 12 of guard 10 and adapter 50 snap-fit together, into the adapter's guard receiving channel 59, in a mechanical interlock via adapter retaining ribs 55 enabling the guard system 10/50 to maintain its position proximate a stoma 31.

Figure 3:
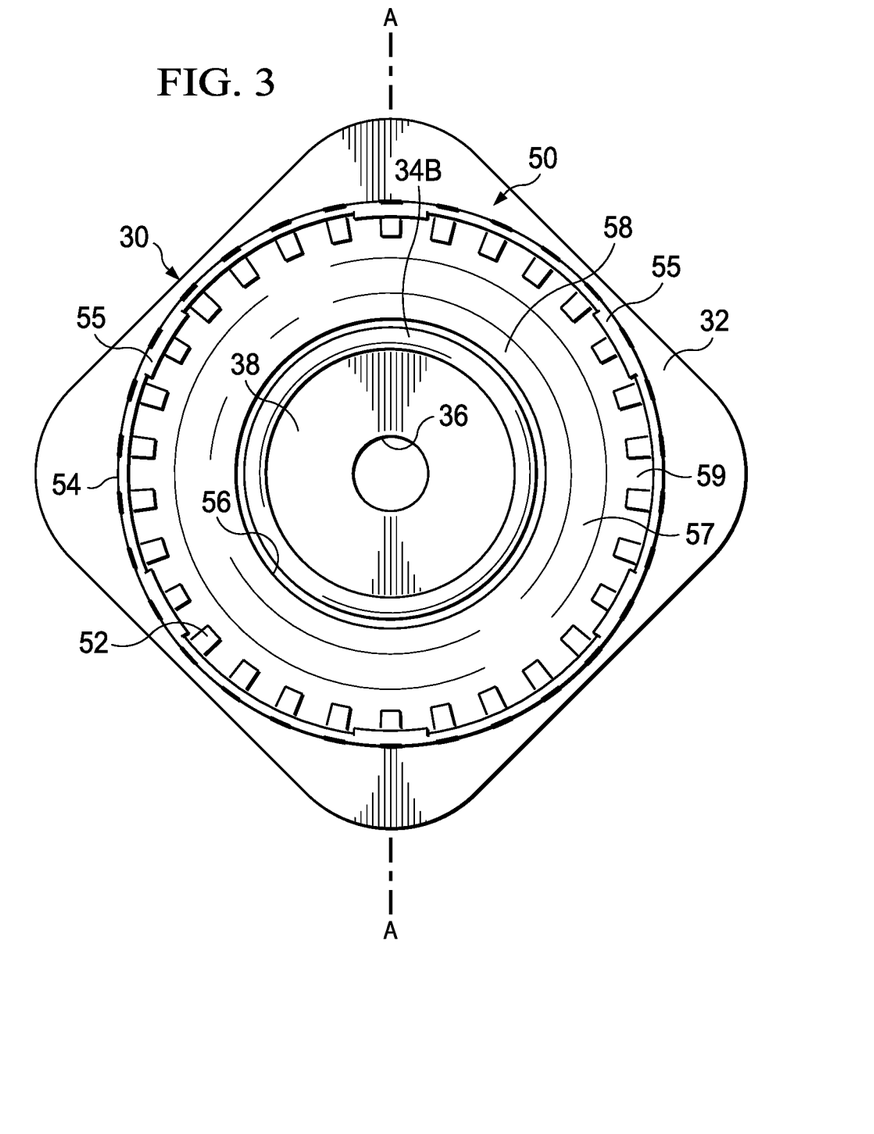
FIG. 3 is a front perspective view of an adapter on the exemplary faceplate of FIGS. 1 & 2.

The body 14 of the guard 10 allows unhindered flow of output. In case liquid output behind the faceplate 30 causes the hydrocolloid adhesive member 38 to loosen from the skin, the hydrocolloid adhesive member 38 may push into a cavity formed by sloping section 57 and support wall 58, and sealed by guard receiving channel 59 that provides a temporary reservoir for effluent, allowing the user time to change the appliance before escape of output occurs. As can be seen in FIG. 3, a guard system 10/50 contacts a faceplate 30 more or less than about ¼ in (0.06 cm) inside the outer periphery of said faceplate. Adapter protrusions 52, on the body-facing side of an adapter 50, create discontinuous contact on a faceplate 30 facilitating blood flow in the non-contact areas and beneficially reducing an itchiness associated with continuous pressure on the skin.

Figure 4:
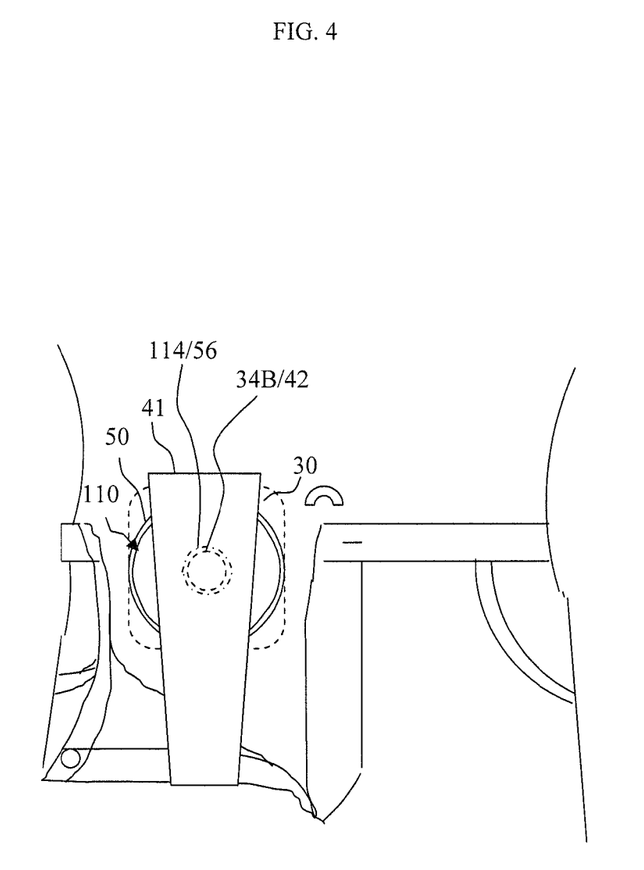
FIG. 4 is an environmental view of a conjoined adapter and insert on the torso of a human.

Referring to FIG. 4, an insert 110 may be used with adapter 50. Together, insert 110 and adapter 50 may be worn temporarily without a guard under form-fitted clothing to aid adhesion of a faceplate 30, and to provide support and stabilization in the peristomal region surrounding a stoma. Insert 110 defines a central aperture 114 that essentially encircles the coupling flanges 34B/42 when in use. Insert 110 is placed proximate faceplate 30 inside adapter 50 so that the faceplate flange resides inside apertures 114/56 (insert and adapter). When pouch 40 is secured to the faceplate, the coupling flanges 34B/42 are essentially surrounded by the edge of aperture 114/56. Coupling flanges 34B/42 inside aperture 114/56 helps insert 110 and adapter 50 maintain its position proximate the stoma.

Figure 5:
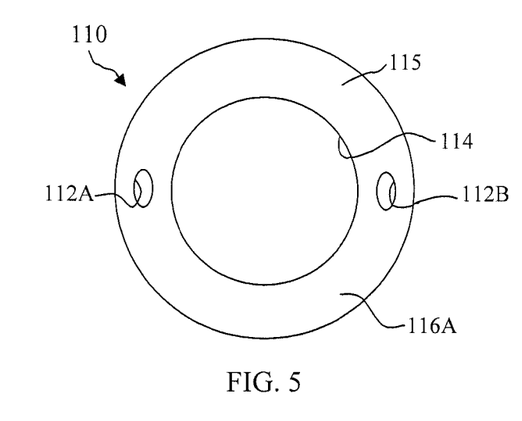
FIG. 5 is a front view of a flat adapter insert.

FIG. 5 illustrates an adapter insert 110 comprising an annular ring 115, having a front side 116A and a back side 116B (shown in FIG. 6), a central aperture 114, and holes 112A and 112B on either side as a means to attach a belt and a flat outer edge 119 that snap-fits into the adapter's guard receiving channel 59 when a guard is not in use. The flat outer edge 119 is flush with the adapter's lip 54 when inserted into the adapter 50 (illustrated in FIG. 8B), and being more or less than about ⅓ in (0.029 in) deep, the approximate depth of the adapter's guard receiving channel 59 measured from the top of lip 54. The insert 110 is applied in the same fashion as the adapter 50 by guiding pouch end 48 in through aperture 114, i.e., in through back side 116B, out through 116A, and lifting the insert 110 up and over upper pouch 41 and insert 110 snap-fits into adapter 50, with front side now adjacent a pouch 40.

The insert 110 for the adapter 50 can be made of any suitable material that can be suitably formed into the desired configurations including a means to attach a security strap. Security straps are known in the art and may be utilized with the insert 110. It should be understood that a security strap is not required when the system is worn under form-fitted clothing, i.e., pants, briefs or underwear, but may be a preferred method of increasing support by a user when looser fitting attire is worn.

The central aperture 114 of insert 110 may otherwise be provided in varied sizes to accommodate various flange sizes of appliances, and preferably in skin tone colors so as not to be noticed under clothing.

Common flange diameters of appliance faceplates generally range more or less than about 1⅞ inches (47 mm), more or less than about 1¾ inches (44 mm), more or less than about 2¼ inches (57 mm), more or less than about 2¾ (70 mm), and more or less than 4.0 inches (100 mm).

An overall diameter of an adapter 50 is configured to rest on the outer tape portion 32 of a faceplate 30. Common and generally square faceplate sizes measured from their peripheral edges may range in diameter approximately more or less than about 1⅞ inch (47 mm) square (infant size), up to more or less than about 4.0 inches (100 mm) square, more or less than about 5.0 inches (127 mm) square, and up to more or less than about 6.0 (152 mm) square, or possibly larger in less common or specially ordered sizes. Circular faceplate diameters or triangular configurations in similar size ranges, as mentioned above, may also be available.

The adapter inserts may be formed of any suitable material of sufficient rigidity and durability to absorb and divert external impact forces. Examples of suitable materials include various hard plastics, polypropylene, high density polyethylene (HDPE), acrylonitrile butadiene styrene (ABS), PC/ABS (polycarbonate/ABS blend), polybutylene terephthalate (PBT), metals, polymers, fiber-reinforced polymers, non-toxic metal (e.g. stainless steel) or other like materials and combinations thereof that may be extruded, vacuum or injection molded, stamped, cast or formed by any suitable process to provide the desired configurations as explained above and exemplified in the figures. Holes for ventilation purposes may be added to the insert. Additionally, padding (i.e. foam, rubber, thermoplastic elastomers (TPE), thermoplastic vulcanizates (TPV) and combinations thereof) may be used on or over any hard surfaces or molded over the entire exterior surface. Added reinforcement may be added by a pattern, grid, or possibly lettering on the front or back side of the insert or any other reinforcement as may be known in the art may be added to provide a rigid and protective device.

Figure 6:
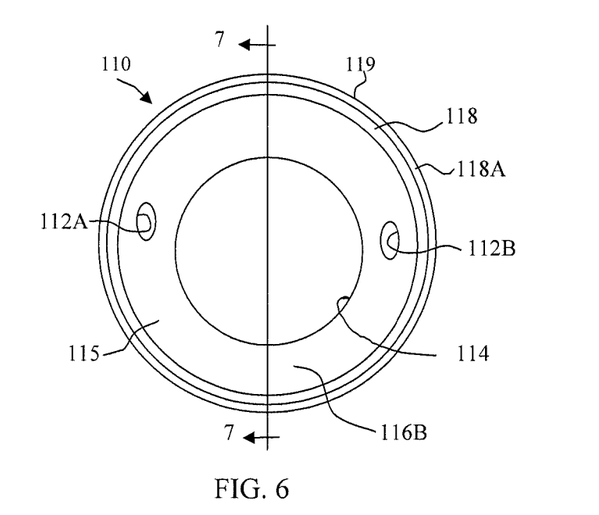
FIG. 6 is a rear view of a flat adapter insert of FIG. 5 showing a reinforced edge.

Referring to FIG. 6, the back side of an adapter insert 110 shown in FIG. 5 is further illustrated. Adapter insert 110 comprises an annular ring 115, having a front side 116A (shown in FIG. 5) and a back side 116B, a central aperture 114, and holes 112A and 112B on either side as a means to attach a belt and a flat outer edge 119 that snap-fits into the adapter's guard receiving channel 59 when a guard is not in use. The outer edge 119 is flush with the adapter's lip 54 when inserted into the adapter 50 and being more or less than about ⅓ in (0.029 in) thick, the approximate depth of the adapter's guard receiving channel 59 measured from the top of lip 54. The back side 116B has reinforcing rings 118 and 118A (or internal vertical reinforcement prong and outer vertical prong) added for strength and rigidity. Reinforcing ring 118A helps form the outer edge 119. The insert 110 is applied in the same fashion as the adapter 50 by guiding pouch end 48 in through aperture 114, i.e., in through back side 116B, out through 116A, and lifting the insert 110 up and over upper pouch 41 and insert 110 snap-fits into adapter 50, with front side now adjacent a pouch 40.

The insert 110 for the adapter 50 can be made of any suitable material that can be suitably formed into the desired configurations including a means to attach a security strap. Security straps are known in the art and may be utilized with the insert 110. It should be understood that a security strap is not required when the system is worn under form-fitted clothing, i.e., pants, briefs or underwear, but may be a preferred method of increasing support by a user when looser fitting attire is worn.

Figure 7:
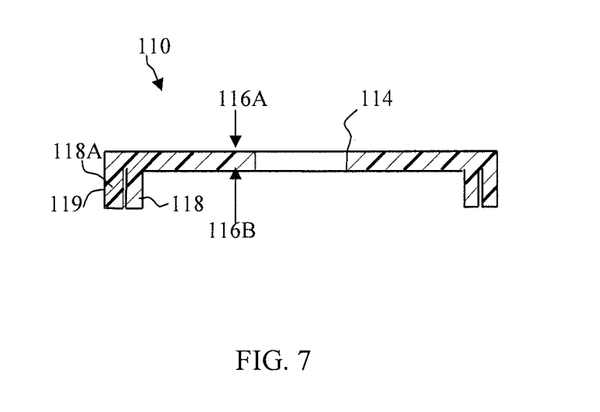
FIG. 7 is a cross-sectional view of the adapter insert of FIG. 6

FIG. 7 illustrates a cross sectional view taken along line 7-7 of FIG. 6. Adapter insert 110 comprises an annular ring 115, having a front side 116A and a back side 116B, a central aperture 114, and holes 112A and 112B (not shown) on either side as a means to attach a belt and a flat outer edge 119 that snap-fits into the adapter's guard receiving channel 59 when a guard is not in use. The outer edge 119 is flush with the adapter's lip 54 when inserted into the adapter 50 and being more or less than about ⅓ in (0.029 in) thick, the approximate depth of the adapter's guard receiving channel 59 measured from the top of lip 54. The back side 116B has reinforcing rings 118 and 118A added for strength and rigidity. Reinforcing ring 118A helps form the outer edge 119. The insert 110 is applied in the same fashion as the adapter 50 by guiding pouch end 48 in through aperture 114, i.e., in through back side 116B, out through 116A, and lifting the insert 110 up and over upper pouch 41 and insert 110 snap-fits into adapter 50, with front side now adjacent a pouch 40.

The insert 110 for the adapter 50 can be made of any suitable material that can be suitably formed into the desired configurations including a means to attach a security strap. Security straps are known in the art and may be utilized with the insert 110. It should be understood that a security strap is not required when the system is worn under form-fitted clothing, i.e., pants, briefs or underwear, but may be a preferred method of increasing support by a user when looser fitting attire is worn.

Figure 8:
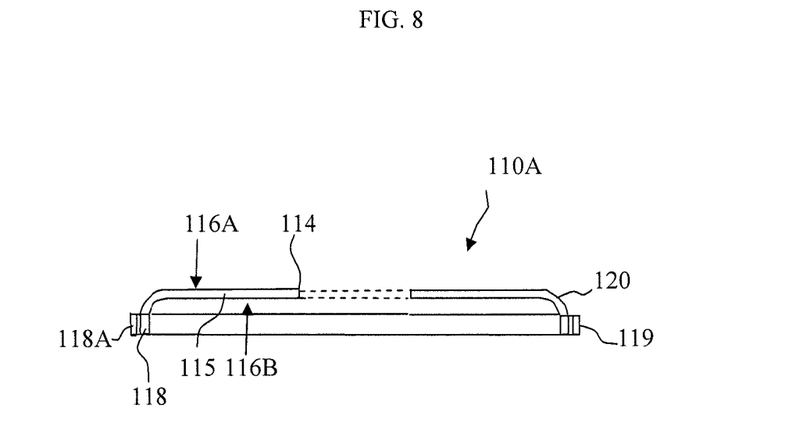
FIG. 8 is a second embodiment of a cross-sectional view of a sloped adapter insert showing space for a reservoir.

A second embodiment for an insert 110A for an adapter is shown in FIG. 8 and comprises a rigid annular ring 115, having a front side 116A and a back side 116B wherein a central aperture 114 is dimensioned to permit a pouch to be inserted therethrough and further having means to connect a security strap by two or more holes adapted to receive a securing strap therethrough or within, or by any means to attach a security strap for the purpose intended. Additional fastening means that would prevent ballooning of a pouch above the waistband of clothing may be in the form of slits, or protrusions or hooks flush with the surface at a 10:00 and 2:00 o'clock position to add a strap, or a hook and loop means to attach for anti-ballooning purposes in this or the flat insert 10.

The insert 110A also comprises a flat outer edge 119 that snap-fits into the adapter guard-receiving channel 59 to maintain a position in the adapter and is alternately not flush with the adapter lip 54. The back side 116B has reinforcing rings 118 and 118A (or internal vertical reinforcement prong and outer vertical prong) added for strength and rigidity. Reinforcing ring 118A helps form the outer edge 119. The annular ring 115 also has a sloped support wall 120 in the case liquid output behind the faceplate 30 causes the hydrocolloid adhesive member 38 to loosen from the skin, the hydrocolloid adhesive member 38 may push into a cavity formed by sloped support wall 120 and is sealed by guard receiving channel 59 as pressure is applied to a faceplate 30 from form-fitted clothing and that provides a temporary reservoir for effluent, allowing the user time to change the appliance before escape of output occurs.

Figure 8A:
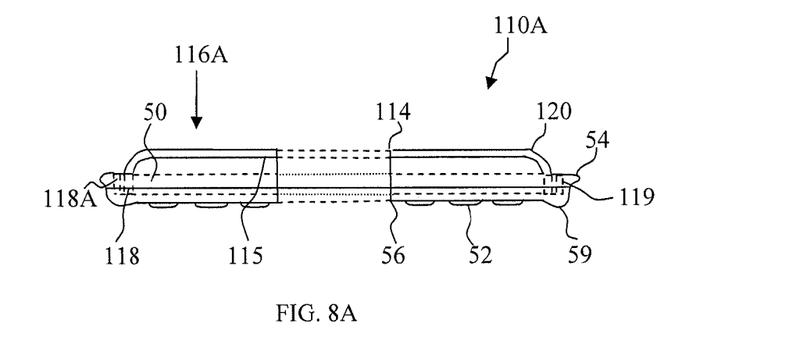
FIG. 8A is a cross-sectional view of a sloped insert placed in an adapter.

FIG. 8A illustrates a cross-sectional view of a sloped insert 110A in place in the adapter 50 showing the sloped insert is not flush with lip 54 of an adapter 50.

The insert comprises a rigid annular ring 115, having a front side 116A and a back side 116B wherein a central aperture 114 is dimensioned to permit a pouch to be inserted therethrough and further having means to connect a security strap by two or more holes adapted to receive a securing strap therethrough or within, or by any means to attach a security strap for the purpose intended. The insert 110A also comprises a flat outer edge 119 that snap-fits into the adapter guard-receiving channel 59 to maintain a position in the adapter and is not flush with the adapter lip 54. The back side 116B has reinforcing rings 118 and 118A (or internal vertical reinforcement prong and outer vertical prong) added for strength and rigidity. Reinforcing ring 118A helps form the outer edge 119. The annular ring 115 also has a sloped support wall 120 in the case liquid output behind the faceplate 30 causes the hydrocolloid adhesive member 38 to loosen from the skin, the hydrocolloid adhesive member 38 may push into a cavity formed by sloped support wall 120 and is sealed by guard receiving channel 59 as pressure is applied to a faceplate 30 from form-fitted clothing and that provides a temporary reservoir for effluent, allowing the user time to change the appliance before escape of output occurs.

Figure 8B:
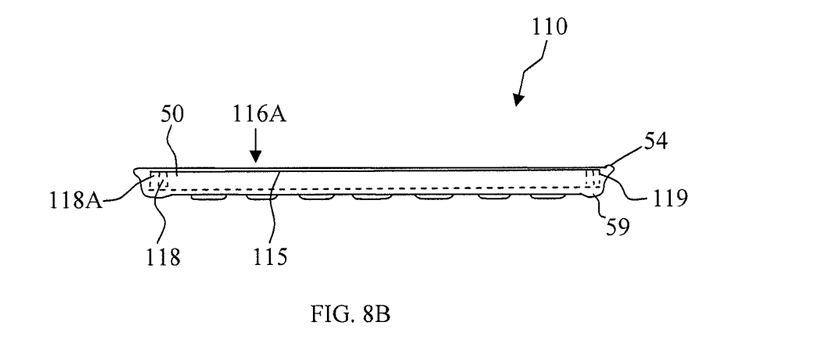
FIG. 8B is a cross-sectional view of a flat insert placed in an adapter.

FIG. 8B illustrates an embodiment wherein adapter 50 and sloped insert 110A do not have a central aperture. There are those ostomates who are able to have a reversal of their condition where a surgically created stoma is re-connected to the intestines allowing the normal function of elimination of bodily wastes. The repaired area of the surgical site may still be susceptible to herniation and a flexible adapter 50 with a flat insert 110 or a sloped insert 110A could be utilized as support for the weakened site until further healing takes place.

Alternately, the inserts, 110 or 110A as exemplified in the figures could be bonded together by any means known in the art to provide a single device and inserts 110 and 110A may be molded over on the entire exterior surface by any process suitable, such as injection molding, extrusion, co-extrusion processes etc., and adjusted to any size or dimensions to accommodate reversal sites other sutured areas on the abdomen that may be susceptible to herniation and may be oblong, square with rounded corners, flattened egg shape, crescent shape or any other shape allowing one the freedom to bend over comfortably and preferably in skin tone colors as to not be seen under clothing. The insert may be formed of any material suitable and selected from any of the above mentioned plastic or metallic materials but preferably a rigid plastic so as not to be detained or detected by devices that detect metal and used for security purposes such as airports, etc., for peace of mind of the wearer.

Colostomates have short term circumstances that allow them to practically wear a bandage over their stoma, without a pouch. Also, there are those ostomates who have reversals, where they no longer have a stoma and may be susceptible to a hernia at the closed site, and may wear this support until the site has had time to heal. The flexible adapter and insert may be worn under form-fitted clothing. The insert may be formed in various sizes or shapes to accommodate any surgical site on the abdomen. No central aperture would be needed in this case.

Figure 9:
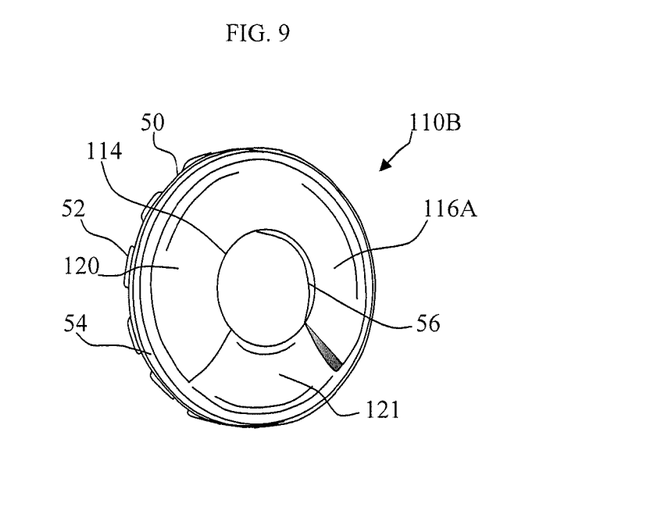
FIG. 9 is a third embodiment of a sloped insert having a recessed flow channel in place in an adapter.
Figure 10:
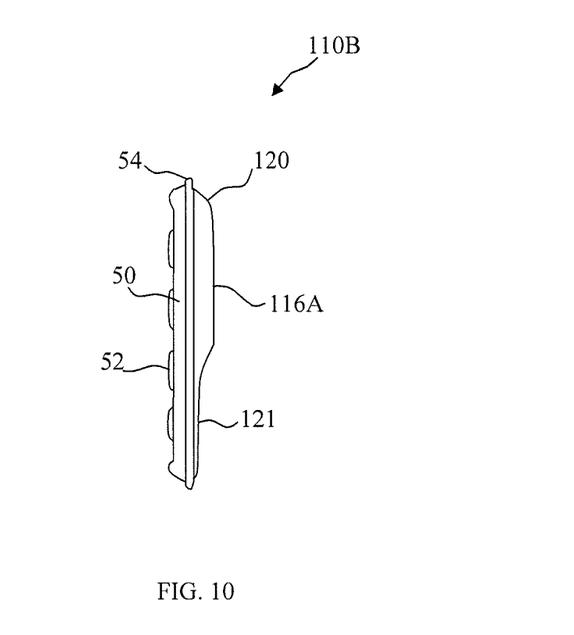
FIG. 10 is a side view of the embodiment of FIG. 9 placed in an adapter.

FIGS. 9 and 10 show a third embodiment of a sloped insert 110B used with an adapter 50 having a recessed flow channel 121 along a portion of the annular ring. Recessed flow channel 121 has two annular edges, an inner edge and an outer edge. The recessed flow channel 121 is abutted by the sloped support wall 120 along the two annular edges. The recessed flow channel 121 allows for improved flow of output near the opening of the stoma 31 and device aperture 114, as can be seen more clearly in FIG. 11.

Figure 11:
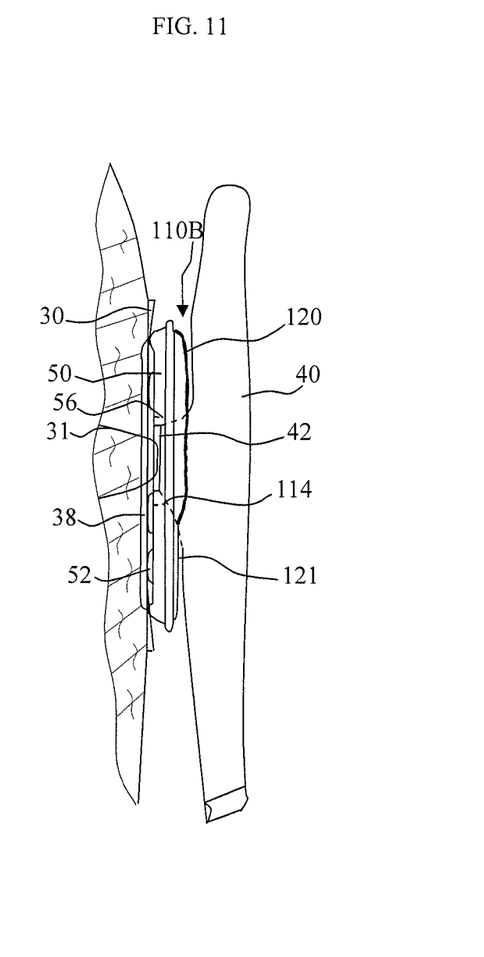
FIG. 11 is a side view of the embodiment of FIG. 9 as worn with an ostomy appliance on the abdomen.

FIG. 11 illustrates how the third embodiment of the device is worn with an ostomy appliance on the abdomen of the wearer.

Figure 12:
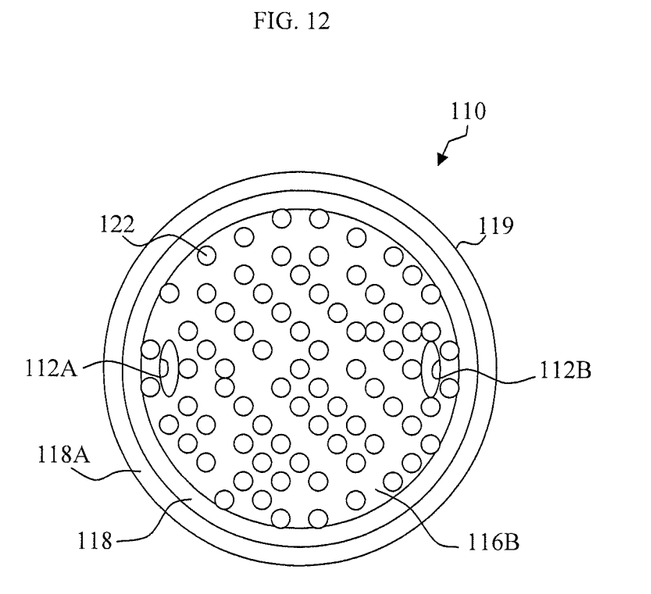
FIG. 12 is a rear view of an alternate embodiment of a sloped insert having a plurality of apertures.

FIG. 12 shows another embodiment wherein a sloped insert 110 has a plurality of apertures 122 for ventilation and is provided over a closed ostomy site for further healing or susceptible to herniation, or for protection against blunt force trauma, clothing, pets, children, etc. As with the previous embodiments, the insert may be adjusted to any size or dimensions to accommodate such sites, or other sutered areas, or worn over bandages with pressure relief dressings to cover and protect those sites on the abdomen from waistbands or clothing or may be worn on other parts of the body and held in place by a security strap or hook and loop fastening means. FIG. 12 does not illustrate a centrally located aperture adapted for the attachment of an ostomy pouch to an ostomy flange, but including the centrally located aperture with this embodiment remains within the scope of the invention.

While preferred embodiments of the invention have been shown and described, modifications thereof can be made by one skilled in the art without departing from the spirit and teachings of the invention. The embodiments described herein are exemplary only, and are not intended to be limiting.

Many variations and modifications of the invention disclosed herein are possible and are within the scope of the invention.

Having described the invention, I claim:

1. An ostomy insert device, comprising:
   an annular ring having a back surface of a substantially horizontal planar shape with an enclosed space and a front surface of a substantially horizontal planar shape on the opposing side from the back surface of said annular ring, said annular ring shaped to insert into an internal lip of an ostomy guard adapter;
   ventilation holes that extend through the back surface and front surface of said annular ring,
   a substantially vertical flat outer edge associated with an exterior edge of the annular ring having an outer vertical prong and an internal vertical reinforcement prong positioned inside said vertical prong adapted to substantially engage with the lip of the ostomy guard adapter; and
   said ostomy insert device having a rigidity to reinforce and stiffen said ostomy guard adapter to aid adhesion of an ostomy faceplate to a peristomal region.

2. The ostomy insert device of claim 1, wherein said annular ring defines belt holes that extend through the back surface and front surface adapted for attachment of a belt.

3. The ostomy insert device of claim 1, wherein said ostomy insert device has a depth the approximate depth of the ostomy guard adapter.

4. The ostomy insert device of claim 1, wherein said ostomy insert device has a depth of about ⅓ inch.

5. The ostomy insert device of claim 1, wherein said substantially vertical flat outer edge further engages with one or more tabs associated with the lip of the ostomy guard adapter.

6. A method of making the ostomy insert device of claim 1, comprising the steps of:
   providing the annular ring;
   adding the ventilation holes through the back surface and front surface of the annular ring; and
   providing the substantially vertical flat outer edge.

7. The method of claim 6, wherein said annular ring defines belt holes that extend through the back surface and front surface adapted for attachment of a belt.

8. The method of claim 6, wherein said ostomy insert device has a depth the approximate depth of the ostomy guard adapter.

9. The method of claim 6, wherein said ostomy insert device has a depth of about ⅓ inch.

10. The method of claim 6, wherein said substantially vertical flat outer edge further engages with one or more tabs associated with the lip of the ostomy guard adapter.

* * * * *